United States Patent
Park et al.

(10) Patent No.: US 9,318,713 B2
(45) Date of Patent: Apr. 19, 2016

(54) ASYMMETRIC FUSED POLYHETEROAROMATIC COMPOUND, ORGANIC THIN FILM INCLUDING THE ASYMMETRIC FUSED POLYHETEROAROMATIC COMPOUND, AND ELECTRONIC DEVICE INCLUDING THE ORGANIC THIN FILM

(71) Applicant: Samsung Electronics Co., Ltd., Suwon-si, Gyeonggi-do (KR)

(72) Inventors: Jeong Il Park, Seongnam-si (KR); Eun Kyung Lee, Seoul (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/541,241

(22) Filed: Nov. 14, 2014

(65) Prior Publication Data

US 2015/0133679 A1    May 14, 2015

(30) Foreign Application Priority Data

Nov. 14, 2013 (KR) .......... 10-2013-0138295
Nov. 11, 2014 (KR) .......... 10-2014-0156415

(51) Int. Cl.
| | | |
|---|---|---|
| H01L 51/00 | (2006.01) | |
| C07D 495/14 | (2006.01) | |
| C07D 495/22 | (2006.01) | |
| H01L 51/05 | (2006.01) | |

(52) U.S. Cl.
CPC .......... *H01L 51/0074* (2013.01); *C07D 495/14* (2013.01); *C07D 495/22* (2013.01); *H01L 51/0541* (2013.01); *H01L 51/0545* (2013.01); *H01L 51/0558* (2013.01)

(58) Field of Classification Search
CPC ................. H01L 51/0541; H01L 51/0074
USPC .............................................. 549/42
See application file for complete search history.

(56) References Cited

U.S. PATENT DOCUMENTS

| | | | |
|---|---|---|---|
| 5,852,204 A | 12/1998 | Miller et al. | |
| 6,013,807 A | 1/2000 | Miller et al. | |
| 7,816,673 B2 | 10/2010 | Park et al. | |
| 8,658,805 B2 | 2/2014 | Park et al. | |
| 8,742,410 B2 | 6/2014 | Park et al. | |
| 2013/0320316 A1 | 12/2013 | Park et al. | |

FOREIGN PATENT DOCUMENTS

| | | |
|---|---|---|
| JP | 2006290192 A | 10/2006 |
| JP | 2007197400 A | 8/2007 |
| JP | 2009141338 A | 6/2009 |
| JP | 2010087408 A | 4/2010 |
| JP | 2010177641 A | 8/2010 |
| JP | 2010177641 A * | 8/2010 |
| JP | 2010177642 A | 8/2010 |
| JP | 2010205982 A | 9/2010 |
| KR | 1020080054553 A | 6/2008 |
| KR | 1020130050266 A | 5/2013 |
| KR | 1020130188629 A | 10/2013 |
| KR | 1020130136938 A | 12/2013 |
| WO | WO-9521170 A1 | 8/1995 |
| WO | WO-2009009790 A1 | 1/2009 |

OTHER PUBLICATIONS

King, Med. Chem. Principle and Practice (1994), pp. 206-208.*
Munir Ahmed, et al. "The direct Bradsher Reaction// Part I. Synthesis of Thiophen Analogues of Linear PolyCyclic Hydrocarbons", Journal of Chemical Society, Perkin Transactions 1: Organic and Bio-Organic Chemistry, pp. 1099-1103 (1973).

* cited by examiner

*Primary Examiner* — Taofiq A Solola
(74) *Attorney, Agent, or Firm* — Harness, Dickey & Pierce, P.L.C.

(57) ABSTRACT

An asymmetric fused polycyclic heteroaromatic compound is represented by the above Chemical Formula 1-1 or Chemical Formula 1-2, and is highly fused due to fusion of greater than or equal to 4 rings.

7 Claims, 4 Drawing Sheets

ASYMMETRIC FUSED POLYHETEROAROMATIC COMPOUND, ORGANIC THIN FILM INCLUDING THE ASYMMETRIC FUSED POLYHETEROAROMATIC COMPOUND, AND ELECTRONIC DEVICE INCLUDING THE ORGANIC THIN FILM

CROSS-REFERENCE TO RELATED APPLICATION

This application claims priority to and the benefit of Korean Patent Application No. 10-2013-0138295 filed in the Korean Intellectual Property Office on Nov. 14, 2013, and Korean Patent Application No. 10-2014-0156415 filed in the Korean Intellectual Property Office on Nov. 11, 2014 the entire contents of which are incorporated herein by reference.

BACKGROUND

1. Field

Example embodiments relate to an asymmetric fused polycyclic heteroaromatic compound, an organic thin film including the same, and an electronic device including the organic thin film.

2. Description of the Related Art

In general, flat display devices, e.g., liquid crystal displays or organic electroluminescent displays, are provided with a variety of thin film transistors (TFTs) to drive them. The TFT may include a gate electrode, source/drain electrodes, and a semiconductor layer that may be activated in response to operation of the gate electrode. The semiconductor layer may include an organic semiconductor material that is controlled by a current between the source electrode and the drain electrode using an applied gate voltage.

Recently, there has been research on a polymer organic material, for example, polythiophene, or a low molecular organic material, for example, pentacene, as an organic semiconductor material to be used for a channel of a thin film transistor. However, the polymer organic material has lower charge mobility but a higher blocking leakage current. On the other hand, the low molecular organic material, for example, pentacene, is reported to have higher charge mobility of greater than or equal to about 3.2 to about 5.0 cm$^2$/Vs but needs expensive vacuum deposition equipment to form a thin film, and thus may not be appropriate in terms of processibility and formation of a larger area.

SUMMARY

Example embodiments provide a heteroaromatic compound, an organic thin film including the same, and an electronic device including the organic thin film, for example, an asymmetric fused polycyclic heteroaromatic compound in which four or more rings are all fused, an organic thin film including the same, and an electronic device including the organic film as a carrier transport layer.

The heteroaromatic compound according to example embodiments has a compact planar structure, and thus may be well packed and stacked among molecules and provide an electronic device having improved electrical characteristics with higher charge mobility.

According to example embodiments, a fused polycyclic heteroaromatic compound is represented by the following Chemical Formula 1-1 or 1-2.

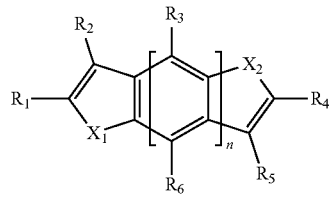

[Chemical Formula 1-1]

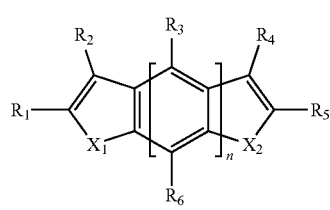

[Chemical Formula 1-2]

In the Chemical Formula 1-1 or 1-2, each of $X_1$ and $X_2$ are independently one of O, S, Se, Te, and N—R$^a$, each of $R_1$ to $R_6$ and R$^a$ are independently one of hydrogen, a substituted or unsubstituted linear or branch $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, a substituted or unsubstituted $C_6$ to $C_{30}$ aryloxy group (—OR$^b$, wherein R$^b$ is a substituted or unsubstituted $C_6$ to $C_{30}$ aryl group), a substituted or unsubstituted $C_4$ to $C_{30}$ cycloalkyl group, a substituted or unsubstituted $C_4$ to $C_{30}$ cycloalkyloxy group (—OR$^c$, wherein R$^c$ is a substituted or unsubstituted $C_4$ to $C_{30}$ cycloalkyl group), a substituted or unsubstituted $C_2$ to $C_{30}$ heteroaryl group, a halogen, and a combination thereof, each of $R_1$ and $R_2$ are independently present or are linked to each other to provide one of a substituted or unsubstituted $C_6$ to $C_{30}$ aromatic ring and a $C_2$ to $C_{30}$ hetero aromatic ring, each of $R_4$ and $R_5$ are independently present or are linked to each other to provide one of a substituted or unsubstituted $C_6$ to $C_{30}$ aromatic ring and a $C_2$ to $C_{30}$ hetero aromatic ring, at least one of $R_1$ and $R_2$, and $R_4$ and $R_5$, are linked to each other to provide one of a substituted or unsubstituted $C_6$ to $C_{30}$ aromatic ring and $C_2$ to $C_{30}$ hetero aromatic ring, and when both the $R_1$ and $R_2$ groups and $R_4$ and $R_5$ groups are linked to each other to provide one of a substituted or unsubstituted $C_6$ to $C_{30}$ aromatic ring and a $C_2$ to $C_{30}$ hetero aromatic ring, a ring including $R_1$ and $R_2$ is different from a ring including $R_4$ and $R_5$, and n is one of 1, 2 and 3.

In addition, a ring provided by linking $R_1$ with $R_2$ and a ring provided by linking $R_4$ with $R_5$ may independently be a substituted or unsubstituted thiophene, a substituted or unsubstituted thienothiophene, a substituted or unsubstituted benzothiophene, a substituted or unsubstituted benzene, a substituted or unsubstituted thienobenzene, a substituted or unsubstituted naphthalene, or a substituted or unsubstituted anthracene.

The fused polycyclic heteroaromatic compound may be one of the fused polycyclic heteroaromatic compounds represented by the following Chemical Formulae 1A to 1L.

[Chemical Formula 1A]
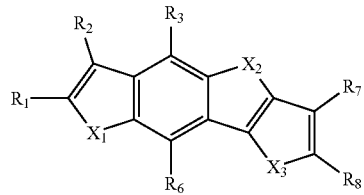
[Chemical Formula 1B]
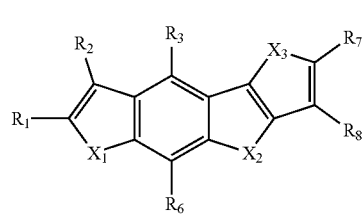
[Chemical Formula 1C]
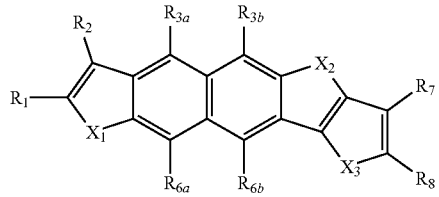
[Chemical Formula 1D]
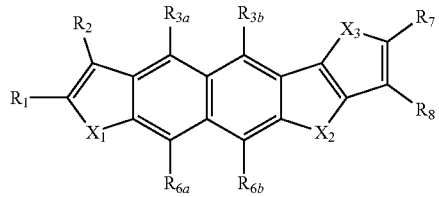
[Chemical Formula 1E]
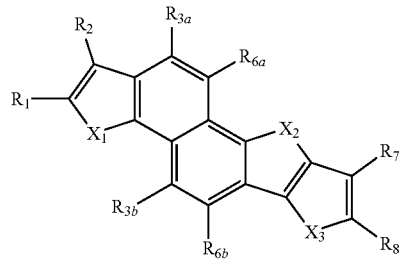
[Chemical Formula 1F]
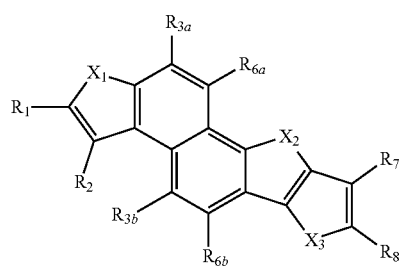
[Chemical Formula 1G]
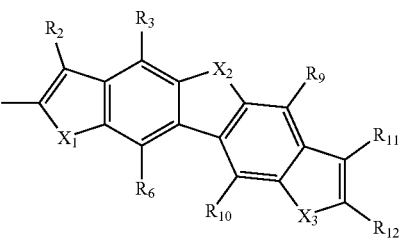
[Chemical Formula 1H]
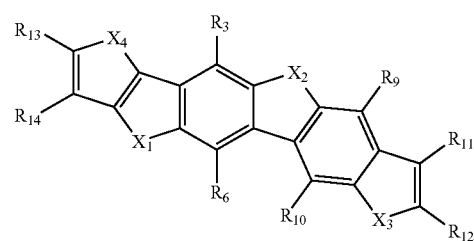
[Chemical Formula 1I]
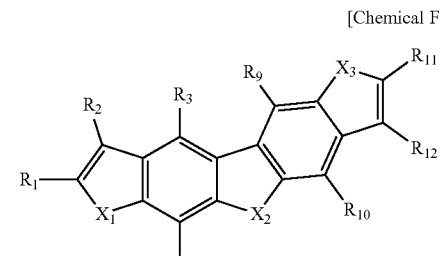
[Chemical Formula 1J]
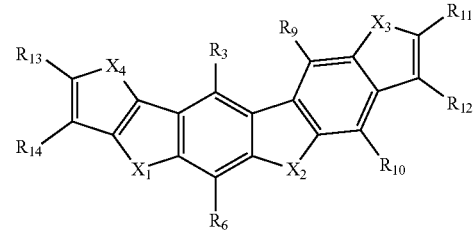
[Chemical Formula 1K]
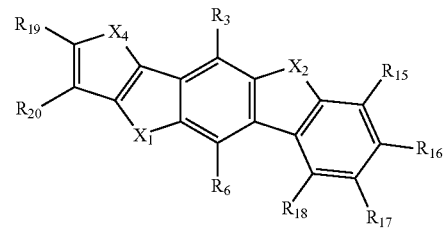
[Chemical Formula 1L]
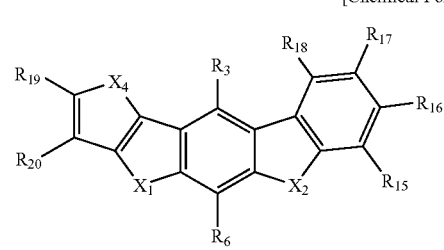

In the Chemical Formulae 1A to 1L, $X_1$, $X_2$, $X_3$, and $X_4$ are independently O, S, Se, Te, or N—$R^a$, and $R_1$ to $R_3$, $R_{3a}$, $R_{3b}$, $R_6$, $R_{6a}$, $R_{6b}$, $R_7$ to $R_{20}$, and $R^a$ are independently a single bond, hydrogen, a substituted or unsubstituted linear or branch $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, a substituted or unsubstituted $C_6$ to $C_{30}$ aryloxy group (—$OR^b$, wherein $R^b$ is a substituted or unsubstituted $C_6$ to $C_{30}$ aryl group), a substituted or unsubstituted $C_4$ to $C_{30}$ cycloalkyl group, a substituted or unsubstituted $C_4$ to $C_{30}$ cycloalkyloxy group (—$OR^c$, wherein $R^c$ is a substituted or unsubstituted $C_4$ to $C_{30}$ cycloalkyl group), a substituted or unsubstituted $C_2$ to $C_{30}$ heteroaryl group, a halogen, or a combination thereof.

The fused polycyclic heteroaromatic compound may have an average molecular weight of about 350 to about 3000.

According to example embodiments, an organic thin film includes the fused polycyclic heteroaromatic compound.

According to example embodiments, an electronic device includes the fused polycyclic heteroaromatic compound.

The electronic device may be one of a transistor, an organic light emitting diode (OLED), a photovoltaic device, a solar cell, a laser device, a memory, and a sensor.

The electronic device may include at least one charge transport layer, and the fused polycyclic heteroaromatic compound may be included in the charge transport layer.

DETAILED DESCRIPTION

Figure 1:
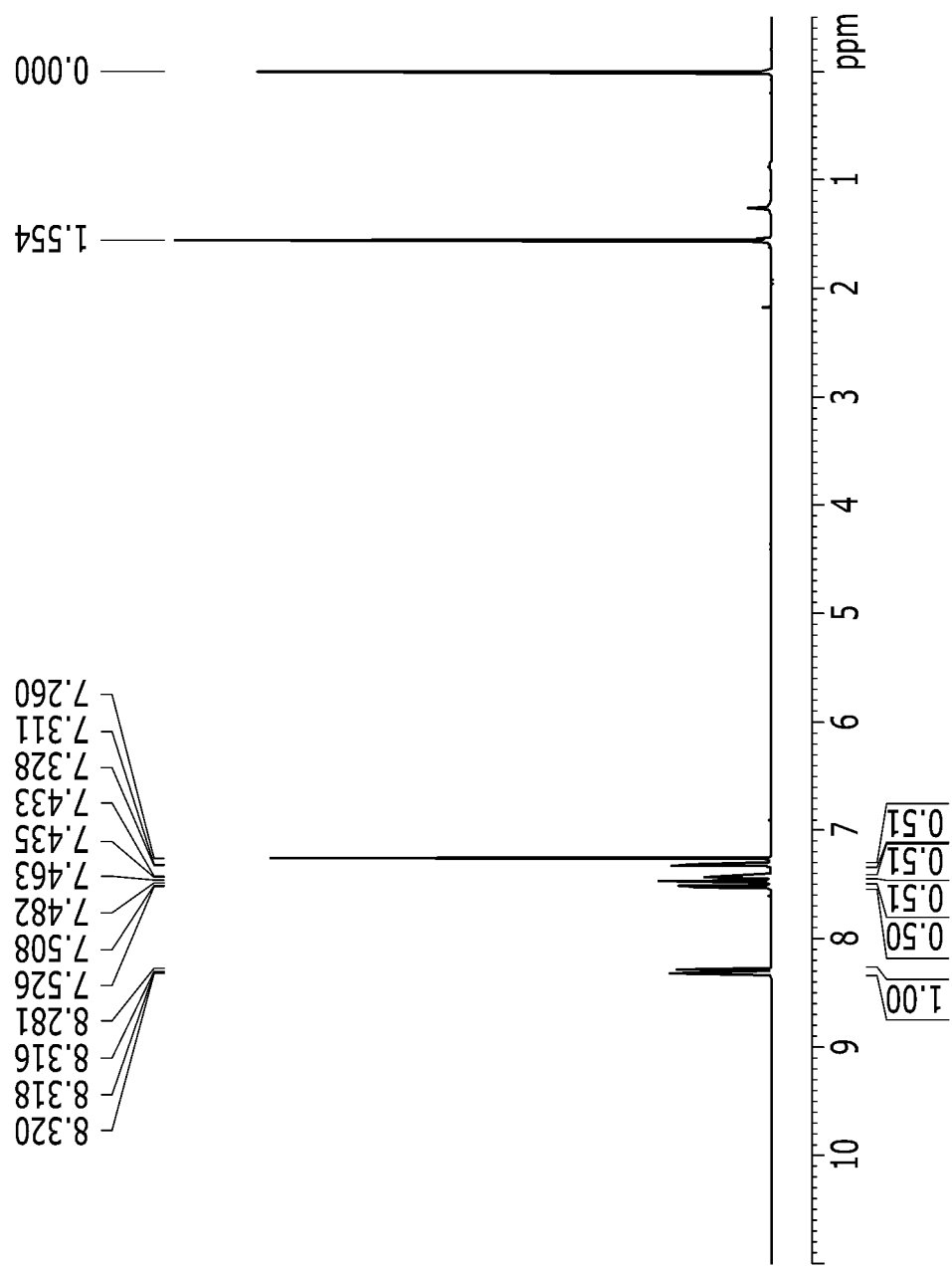
FIG. 1 is a $^1H$ NMR graph showing the compound (4) obtained in Example 1.

The present disclosure will be described more fully hereinafter with reference to the accompanying drawings, in which example embodiments are shown. However, this disclosure may be embodied in many different forms, and is not construed as limited to the example embodiments set forth herein.

In the drawings, the thickness of layers, films, panels, regions, etc., are exaggerated for clarity.

It will be understood that when an element such as a layer, film, region, or substrate is referred to as being "on" another element, it may be directly on the other element or intervening elements may also be present. In contrast, when an element is referred to as being "directly on" another element, there are no intervening elements present.

It should be understood that, although the terms first, second, third, etc. may be used herein to describe various elements, components, regions, layers and/or sections, these elements, components, regions, layers, and/or sections should not be limited by these terms. These terms are only used to distinguish one element, component, region, layer, or section from another region, layer, or section. Thus, a first element, component, region, layer, or section discussed below could be termed a second element, component, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing.

Unless otherwise defined, all terms used in the specification (including technical and scientific terms) may be used with meanings commonly understood by a person having ordinary knowledge in the art. Further, unless explicitly defined otherwise, the terms defined in a generally-used dictionary are not ideally or excessively interpreted. In addition, unless explicitly described to the contrary, the word "include" and variations such as "includes" or "including" will be understood to imply the inclusion of stated elements but not the exclusion of any other elements throughout the specification.

As used herein, the term "combination thereof" refers to a mixture, a stacked structure, a composite, and/or an alloy.

As used herein, when a definition is not otherwise provided, the term "hetero" may refer to one including 1 to 4 heteroatoms selected from N, O, S, Si, and P. The total number of ring members may be 3 to 10. If multiple rings are present, each ring is independently aromatic, saturated, or partially unsaturated, and multiple rings, if present, may be fused, pendant, spirocyclic, or a combination thereof. The term "heterocycloalkyl group" may be at least one non-aromatic ring including a heteroatom, and the term "heteroaryl group" may be at least one aromatic ring including a heteroatom. Non-aromatic and/or carbocyclic rings may also be present in a heteroaryl group, provided that at least one ring is both aromatic and contains a ring member that is a heteroatom.

As used herein, when a definition is not otherwise provided, the term "alkyl group" may be a linear or branched saturated monovalent hydrocarbon group (e.g., a methyl group, an ethyl group, a propyl group, an isobutyl group, a sec-butyl group, a tert-butyl group, a pentyl group, an isoamyl group, and/or a hexyl group).

The term "alkenyl group" may refer to a linear or branched saturated monovalent hydrocarbon group including at least one carbon-carbon double bond (e.g., an ethenyl group).

The term "alkynyl group" may refer to a linear or branched saturated monovalent hydrocarbon group including at least one carbon-carbon triple bond (e.g., ethynyl group).

The term "alkoxy group" may refer to an alkyl group that is linked via an oxygen, e.g., a methoxy, an ethoxy, and a sec-butyloxy group.

The term "aryl group" may refer to a monovalent functional group formed by the removal of one hydrogen atom from one or more rings of an arene, e.g., phenyl or naphthyl. The arene may refer to a hydrocarbon having an aromatic ring, and includes monocyclic and polycyclic hydrocarbons wherein the additional ring(s) of the polycyclic hydrocarbon may be aromatic or nonaromatic.

The term "aryloxy group" may refer to an aryl group that is linked via an oxygen, and the aryl group is the same as described above.

The "arylalkyl group" may refer to an aryl group where at least one hydrogen is substituted with a lower alkylene, e.g., methylene, ethylene, and/or propylene. For example, the "arylalkyl group" may be a benzyl group or a phenylethyl group.

The term "cycloalkyl group" may refer to a monovalent functional group having one or more saturated rings in which all ring members are carbon, e.g., a cyclopentyl group and a cyclohexyl group.

The term "cycloalkenyl group" may refer to a monovalent functional group including at least one ring having a carbon-carbon double bond, wherein all ring members are carbon, e.g., a cyclopentenyl group or a cyclohexenyl group.

The term "cycloalkynyl group" may refer to a stabilized aliphatic monocyclic or polycyclic functional group including at least one carbon-carbon triple bond.

The term "heteroarylalkyl group" may refer to the alkyl group defined above where at least one hydrogen is substituted with a heteroaryl group.

The term "alkylheteroaryl group" may refer to the heteroaryl group defined above where at least one hydrogen is substituted with an alkyl group.

As used herein, when a definition is not otherwise provided, the term "aromatic ring" refers to a functional group in which all atoms in the cyclic functional group have a p-orbital, wherein these p-orbitals are conjugated. For example, the aromatic ring may be a $C_6$ to $C_{20}$ aryl group.

As used herein, when a definition is not otherwise provided, the term "heteroaromatic ring" refers to a functional group including a heteroatom selected from N, O, and S in a ring in which all atoms in the cyclic functional group have a p-orbital, wherein the p-orbital is conjugated. For example, the heteroaromatic ring may be a $C_2$ to $C_{20}$ heteroaryl group.

As used herein, when a definition is not otherwise provided, the term "alicyclic ring" may refer to a non-conjugated ring, for example, a $C_3$ to $C_{20}$ cycloalkyl group, a $C_3$ to $C_{20}$ heterocycloalkyl group, a $C_3$ to $C_{20}$ cycloalkenyl group, and/or a $C_3$ to $C_{20}$ heterocycloalkenyl group.

As used herein, when a definition is not otherwise provided, the term "substituted" means that a compound or group is substituted with at least one substituent selected independently from a halogen (—F, —Cl, —Br, or —I), a $C_1$ to $C_{30}$ linear or branched alkyl group, for example, a $C_1$ to $C_{10}$ linear or branched alkyl group, a $C_2$ to $C_{30}$ linear or branched alkenyl group, for example, a $C_2$ to $C_{10}$ linear or branched alkenyl group, a $C_2$ to $C_{30}$ linear or branched alkynyl group, for example, a $C_2$ to $C_{10}$ linear or branched alkynyl group, a $C_6$ to $C_{30}$ aryl group, for example, a $C_6$ to $C_{12}$ aryl group, a $C_2$ to $C_{30}$ heteroaryl group, for example, a $C_2$ to $C_{12}$ heteroaryl group, a $C_3$ to $C_{30}$ cycloalkyl group, a $C_1$ to $C_{20}$ fluoroalkyl group, a $C_1$ to $C_{20}$ perfluoroalkyl group ($C_nF_{2n+i}$), a $C_1$ to $C_{30}$ linear or branched alkoxy group, a $C_3$ to $C_{30}$ cycloalkoxy group, a $C_2$ to $C_{30}$ linear or branched alkoxyalkyl group, a $C_4$ to $C_{30}$ cycloalkoxyalkyl group, a cyano group, an amino group (—NRR', wherein R and R' are independently hydrogen or a $C_1$ to $C_{10}$ alkyl group), an amidino group (—C(=NH)NH$_2$), a nitro group (—NO$_2$), an amide group (—C(=O)N(H)R, wherein R is hydrogen or a $C_1$ to $C_{10}$ alkyl group), an aldehyde group (—C(=O)H), a hydroxyl group (—OH), a sulfonyl group (—S(=O)$_2$R, wherein R is independently hydrogen or a $C_1$ to $C_{10}$ alkyl group), and a carbamate group (—NH$_2$C(=O)OR, wherein R is a $C_1$ to $C_{10}$ alkyl group) instead of hydrogen, provided that the substituted atom's normal valence is not exceeded.

Hereinafter, a fused polycyclic heteroaromatic compound according to example embodiments is described.

According to example embodiments, 4 or more rings are fused to each other to provide an asymmetric fused polycyclic heteroaromatic compound having a compact planar structure represented by the following Chemical Formula 1-1 or 1-2.

[Chemical Formula 1-1]

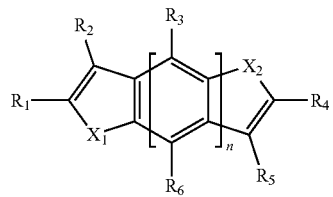

[Chemical Formula 1-2]

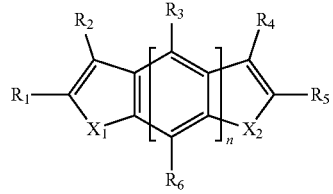

In the Chemical Formula 1-1 or 1-2, each of $X_1$ and $X_2$ are independently one of O, S, Se, Te, and N—$R^a$, each of $R_1$ to $R_6$ and $R^a$ are independently one of hydrogen, a substituted or unsubstituted linear or branch $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, a substituted or unsubstituted $C_6$ to $C_{30}$ aryloxy group (—OR$^b$, wherein R$^b$ is a substituted or unsubstituted $C_6$ to $C_{30}$ aryl group), a substituted or unsubstituted $C_4$ to $C_{30}$ cycloalkyl group, a substituted or unsubstituted $C_4$ to $C_{30}$ cycloalkyloxy group (—OR$^c$, wherein R$^c$ is a substituted or unsubstituted $C_4$ to $C_{30}$ cycloalkyl group), a substituted or unsubstituted $C_2$ to $C_{30}$ heteroaryl group, a halogen, and a combination thereof, each of $R_1$ and $R_2$ are independently present or are linked to each other to provide one of a substituted or unsubstituted $C_6$ to $C_{30}$ aromatic ring and a $C_2$ to $C_{30}$ hetero aromatic ring, each of $R_4$ and $R_5$ are independently present or are linked to each other to provide one of a substituted or unsubstituted $C_6$ to $C_{30}$ aromatic ring and a $C_2$ to $C_{30}$ hetero aromatic ring, at least one of $R_1$ and $R_2$, and $R_4$ and $R_5$, are linked to each other to provide one of a substituted or unsubstituted $C_6$ to $C_{30}$ aromatic ring and $C_2$ to $C_{30}$ hetero aromatic ring, and when both the $R_1$, and $R_2$ groups and $R_4$ and $R_5$ groups are linked to each other to provide one of a substituted or unsubstituted $C_6$ to $C_{30}$ aromatic ring and a $C_2$ to $C_{30}$ hetero aromatic ring, a ring including $R_1$ and $R_2$ is different from a ring including $R_4$ and $R_5$, and n is one of 1, 2, and 3.

The fused heteroaromatic compound has a compact planar structure and may be well stacked among molecules, and thus may be used to prepare an organic semiconductor material having higher mobility by well conjugating the molecules. As the number of a fused cycle is increased, a compound is not easily synthesized due to increased flatness but decreased dissolution.

However, an orbital overlap among molecules is maximized or increased by condensation-reacting at least a core in the disclosure. The core basically has an asymmetric structure in which an aromatic ring is fused with a hetero aromatic ring as shown in Chemical Formula 1-1 or 1-2. The fused heteroaromatic compound may be easily synthesized to have various structures by using an asymmetric material without deteriorating flatness much compared with a symmetric organic semiconductor material as shown in the following Chemical Formulae 1A to 1 L.

The fused polycyclic heteroaromatic compound according to example embodiments may have an average molecular weight of about 350 to about 3000.

In the Chemical Formula 1-1 or 1-2, Ar may be a substituted or unsubstituted benzene, a substituted or unsubstituted naphthalene, or a substituted or unsubstituted anthracene.

In addition, a ring provided by linking $R_1$ with $R_2$ and a ring provided by linking $R_4$ with $R_5$ may independently be a substituted or unsubstituted thiophene, a substituted or unsubstituted thienothiophene, a substituted or unsubstituted benzothiophene, a substituted or unsubstituted benzene, a substituted or unsubstituted thienobenzene, a substituted or unsubstituted naphthalene, or a substituted or unsubstituted anthracene.

The fused polycyclic heteroaromatic compound may be one of the fused polycyclic heteroaromatic compounds represented by the following Chemical Formulae 1A to 1 L.

[Chemical Formula 1A]

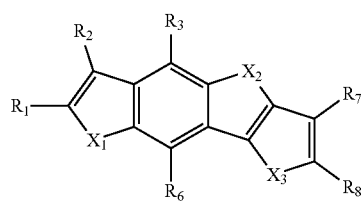

[Chemical Formula 1B]

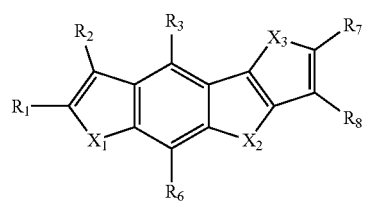

[Chemical Formula 1C]

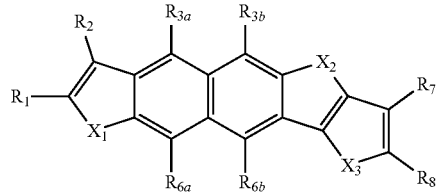

[Chemical Formula 1D]

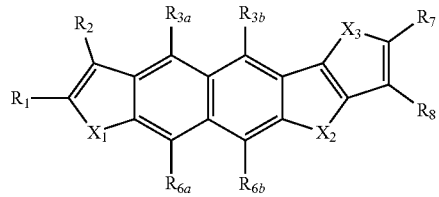

[Chemical Formula 1E]

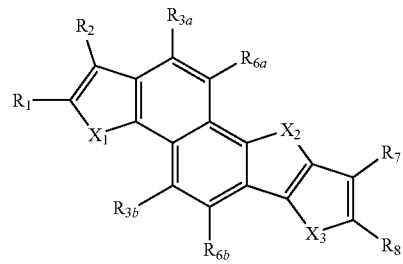

[Chemical Formula 1F]

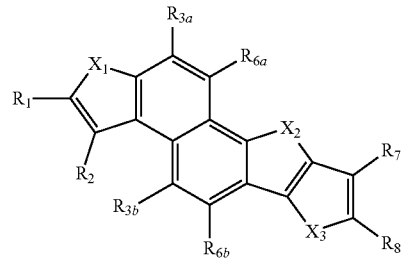

[Chemical Formula 1G]

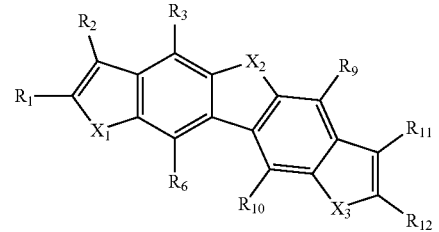

[Chemical Formula 1H]

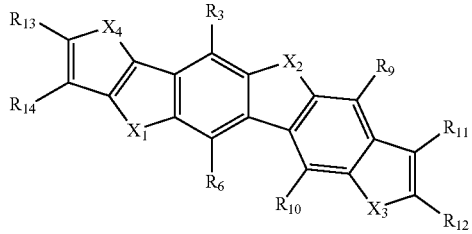

[Chemical Formula 1I]

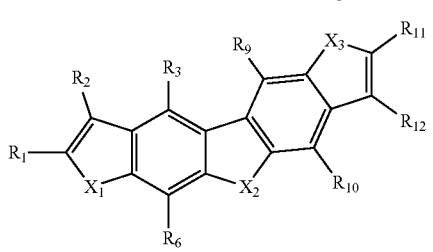

[Chemical Formula 1J]

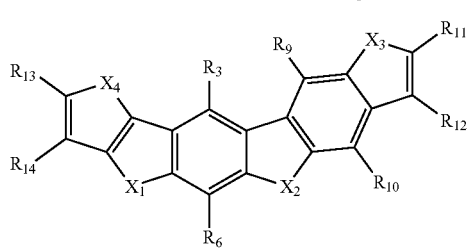

[Chemical Formula 1K]

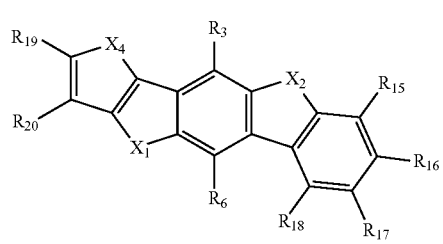

[Chemical Formula 1L]

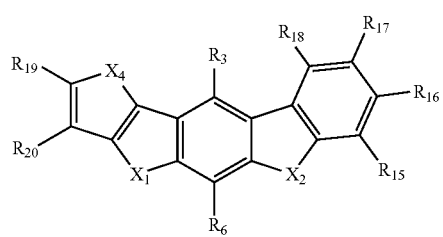

In the Chemical Formulae 1 A to 1 L, each of $X_1$, $X_2$, $X_3$, and $X_4$ are independently one of O, S, Se, Te, and N—$R^a$, and each of $R_1$ to $R_3$, $R_{3a}$, $R_{3b}$, $R_6$, $R_{6a}$, $R_{6b}$, $R_7$ to $R_{20}$, and $R^a$ are independently one of a single bond, hydrogen, a substituted or unsubstituted linear or branched $C_1$ to $C_{30}$ alkyl group, a substituted or unsubstituted $C_7$ to $C_{30}$ arylalkyl group, a substituted or unsubstituted $C_6$ to $C_{30}$ aryl group, a substituted or unsubstituted $C_1$ to $C_{30}$ alkoxy group, a substituted or unsubstituted $C_6$ to $C_{30}$ aryloxy group (—$OR^b$, wherein $R^b$ is a substituted or unsubstituted $C_6$ to $C_{30}$ aryl group), a substituted or unsubstituted $C_4$ to $C_{30}$ cycloalkyl group, a substituted or unsubstituted $C_4$ to $C_{30}$ cycloalkyloxy group (—$OR^c$, wherein $R^c$ is a substituted or unsubstituted $C_4$ to $C_{30}$ cycloalkyl group), a substituted or unsubstituted $C_2$ to $C_{30}$ heteroaryl group, a halogen, and a combination thereof.

Specific examples of the asymmetric fused polycyclic heteroaromatic compound may be the following compounds (1) to (13).

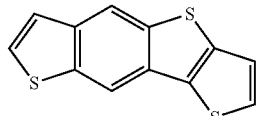

(1)

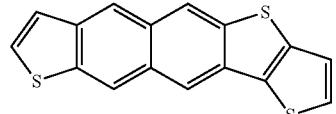

(2)

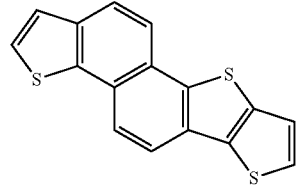

(3)

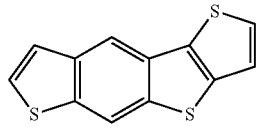

(4)

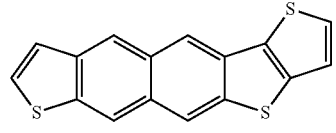

(5)

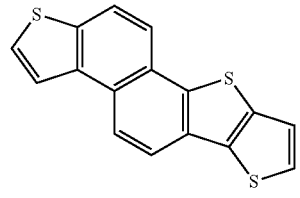

(6)

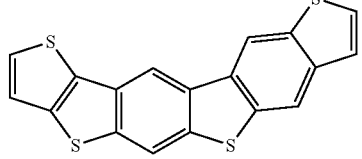

(7)

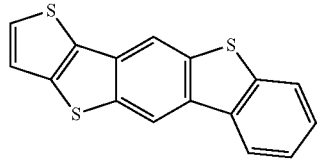

(8)

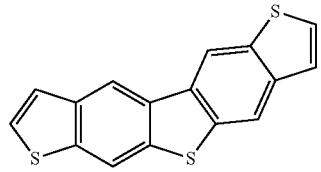

(9)

-continued

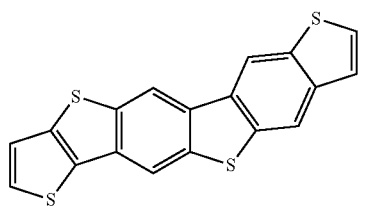
(10)

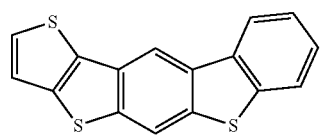
(11)

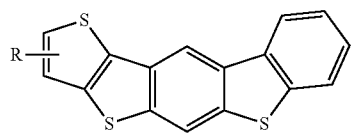
(12)

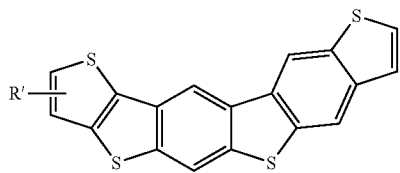
(13)

R of the compounds (12) and R' of the compound (13) may be independently a C1 to C20 linear or branched alkyl group.

The reorganization energy of compounds (1), (4), (8), and (11) among the compounds (1) to (13) is calculated by using the Gaussian 03 program in DFT B3PW91 6-311G+(d,p) level, and the results are shown in the following Table 1. For comparison, the reorganization energy of the following compounds ref-1 and ref-2 is also shown in Table 1.

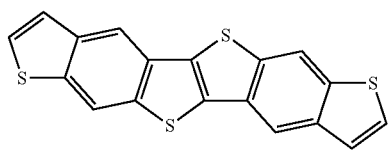
ref-1

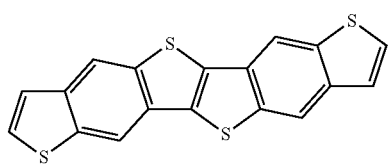
ref-2

TABLE 1

| Compounds | $E_{HOMO}$ (eV) | $E_{LUMO}$ (eV) | ΔE (eV) | Reorganization Energy (eV) | Expectation mobility (cm$^2$/Vs) |
|---|---|---|---|---|---|
| Compound ref-1 | −5.61 | −1.76 | 3.84 | 0.135 | 0.86 |
| Compound ref-2 | −5.57 | −1.99 | 3.57 | 0.162 | 0.90 |
| Compound (1) | −5.72 | −1.68 | 4.04 | 0.197 | 1.49 |
| Compound (4) | −5.75 | −1.53 | 4.21 | 0.136 | 2.37 |
| Compound (8) | −5.81 | −1.84 | 3.97 | 0.164 | 1.43 |
| Compound (11) | −5.77 | −1.65 | 4.12 | 0.182 | 0.99 |

As shown in Table 1, compounds (1), (4), (8), and (11) have larger expectation mobility than compounds ref-1 and ref-2. From the results, the compounds (1), (4), (8), and (11) are expected to have improved charge mobility compared with the compounds ref-1 and ref-2.

The asymmetric fused polycyclic heteroaromatic compound according to example embodiments may be prepared according to a general method, for example, chemical or electrochemical oxidation synthesis, which is a representative method of polymerizing an aromatic compound or a heteroaromatic compound, or condensation polymerization using a compound of an organic transition element, for example, nickel or palladium.

For example, the compound represented by the Chemical Formula 1-1 or Chemical Formula 1-2 may be obtained by a cyclization reaction of an intermediate compound represented by the following Chemical Formula 2. The cyclization reaction may be performed by the method described in, for example, J. Org. Chem. 2005, 70, 4502-4505.

[Chemical Formula 2]

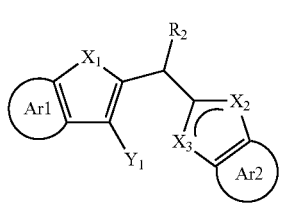

In the Chemical Formula 2,
each of $X_1$, $X_2$, $X_3$, $R_1$, and $R_2$ are the same as in Chemical Formula 1, and $Y_1$ is one of a carbonyl group (—C(=O)R$^d$, wherein R$^d$ is a substituted or unsubstituted $C_1$ to $C_{30}$ alkyl group) and a halogen (e.g., —Br). For example, in Chemical Formula 1B, $X_1$, the fused polycyclic heteroaromatic compound where $X_2$ and $X_3$ are S and $R_1$, $R_2$, $R_3$, $R_6$, $R_7$, and $R_8$ are hydrogen may be synthesized according to the following Reaction Scheme 1, but is not specifically limited thereto.

Hereinafter, the present disclosure is illustrated in more detail with reference to examples. However, these are examples, and the present disclosure is not limited thereto.

EXAMPLE 1

Synthesis of Compound (4)

[Reaction Scheme 1]

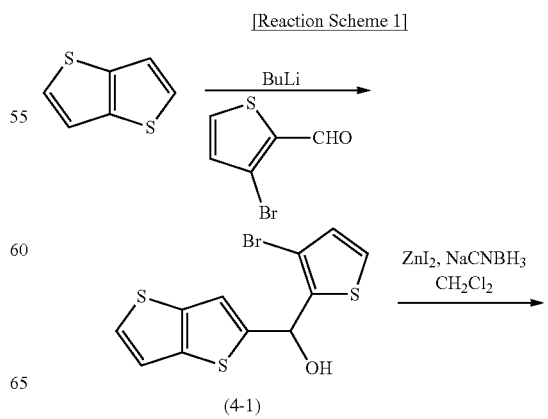
(4-1)

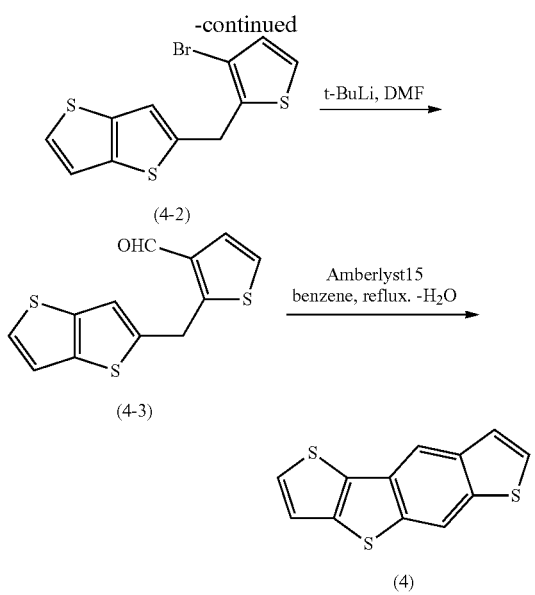

Synthesis of Intermediate (4-1):

Thienothiophene (thieno[3,2:b]thiophene, 5.84 g, 41.65 mmol) is dissolved in 500 mL of dry ether, the solution is added in a dropwise fashion to 100 mL of a dry ether solution including butyl lithium (2.5 M in 25 mL of a hexane solution) cooled down to 0° C., and the mixture is gradually heated up to room temperature and then agitated for 2 hours. Then, 3-bromothiophene-2-aldehyde (10.34 g, 54.14 mmol) is added in a dropwise fashion to the murky solution, and the mixture is agitated overnight. 100 mL of an ammonium chloride-saturated solution is added thereto, and a material precipitated therein is filtered and rinsed several times with water and ether, obtaining an intermediate (4-1) (a yield of 75%).

$^1$H NMR (300 MHz, CDCl$_3$): δ ppm 7.33 (d, 1H), 7.28 (d, 2H), 7.21 (d, 1H), 6.98 (d, 1H), 6.41 (d, 1H), 2.81 (d, 1H); $^{13}$C NMR (75.5 MHz, CDCl$_3$): δ ppm 147.5, 141.1, 139.1, 138.4, 130.0, 127.3, 125.7, 119.6, 117.6, 108.6, 68.7.

Synthesis of Intermediate (4-2):

The intermediate (4-1) (2.86 g, 9.07 mmol) is dissolved in 300 mL of dichloromethane (CH$_2$Cl$_2$), and ZnI$_2$ (4.63 g, 14.51 mmol) and NaCNBH$_3$ (3.99 g, 63.5 mmol) are slowly added thereto. The mixture is agitated at room temperature for 24 hours and then passed through a Celite pad. The filtered solution is respectively rinsed with the ammonium chloride-saturated solution and water, dried with MgSO$_4$, and concentrated under a reduced pressure, obtaining a yellow oil. This material is purified through silica chromatography, obtaining an intermediate (4-2) (a yield of 80%).

$^1$H NMR (300 MHz, CDCl$_3$): δ ppm 7.32 (d, 1H), 7.21 (m, 2H), 7.09 (s, 1H), 6.97 (d, 1H), 4.38 (s, 2H); $^{13}$C NMR (75.5 MHz, CDCl$_3$): δ ppm 143.8, 138.6, 138.3, 137.0, 130.0, 126.2, 124.5, 119.5, 117.9, 109.7, 30.7.

Synthesis of Intermediate (4-3):

A THF solution (100 mL) prepared by dissolving the intermediate (4-2) (6.34 g, 21.2 mmol) is slowly added in a dropwise fashion to an ether solution (200 mL) including t-butyl lithium (31.78 mmol) dissolved therein and cooled down to −78° C. The mixture is agitated at −78° C. for about 30 minutes, DMF (2.32 g) is added thereto, and the resulting mixture is again agitated for about 2 hours. When the reaction is terminated by pouring water thereinto, 200 mL of ethyl acetate is added thereto and rinsed with water and brine to obtain an organic layer, and the organic layer is dried with MgSO$_4$ and concentrated under a reduced pressure, obtaining a colorless oil. This material is purified through silica chromatography, obtaining an intermediate (4-3) (a yield of 70%).

$^1$H NMR (300 MHz, CDCl$_3$): δ ppm 10.1 (s, 1H), 7.39 (s, 1H), 7.29 (d, 1H), 7.15 (m, 2H), 7.06 (s, 1H), 4.74 (s, 2H)

Synthesis of Compound (4):

The intermediate (4-3) (0.44 g) is dissolved in 30 mL of benzene, Amberlyst 15 (0.5 g) is added thereto, and water therein is removed by using a Dean-Stark trap while the mixture is agitated and refluxed. About 24 hours later, a yellow solid is precipitated. The yellow solid of a desired compound (4) is obtained by lowering the temperature down to room temperature, precipitating Amberlyst 15, and filtering the solid after skimming a floating material (a yield of 60%). FIG. 1 is a $^1$H NMR graph confirming that the resultant is the compound (4).

$^1$H NMR (300 MHz, CDCl$_3$): δ ppm 8.31 (d, 2H), 7.51 (d, 1H), 7.47 (d, 1H), 7.43 (d, 1H), 7.32 (d, 1H); $^{13}$C NMR (75.5 MHz, CDCl$_3$): δ ppm 140.2, 137.7, 137.6, 137.0, 134.3, 130.5, 127.9, 126.5, 123.6, 120.6, 117.2, 115.0, 29.7 (See FIG. 1).

EXAMPLE 2

Synthesis of Compound (12')

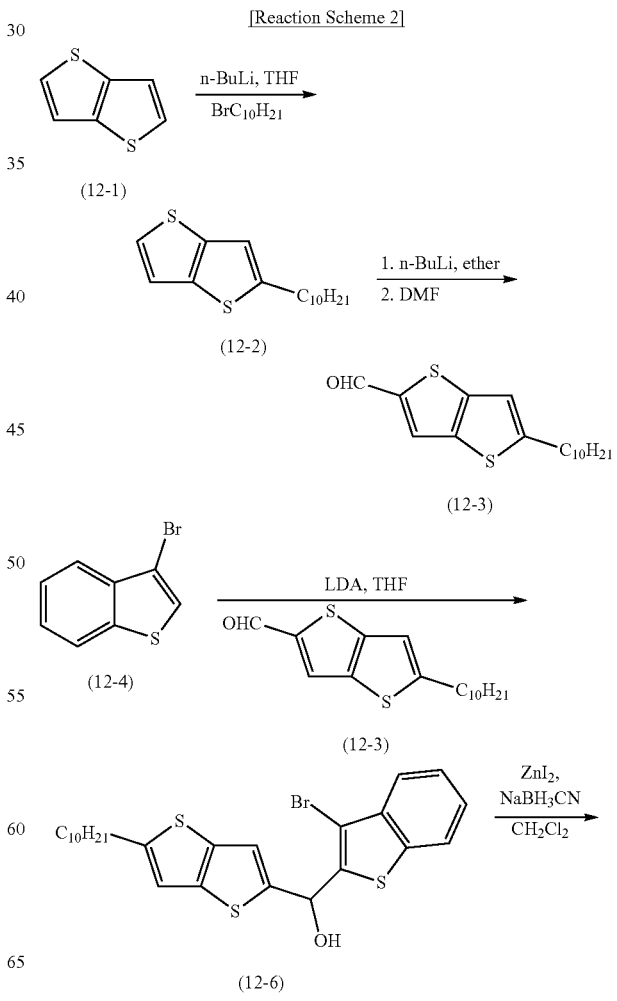

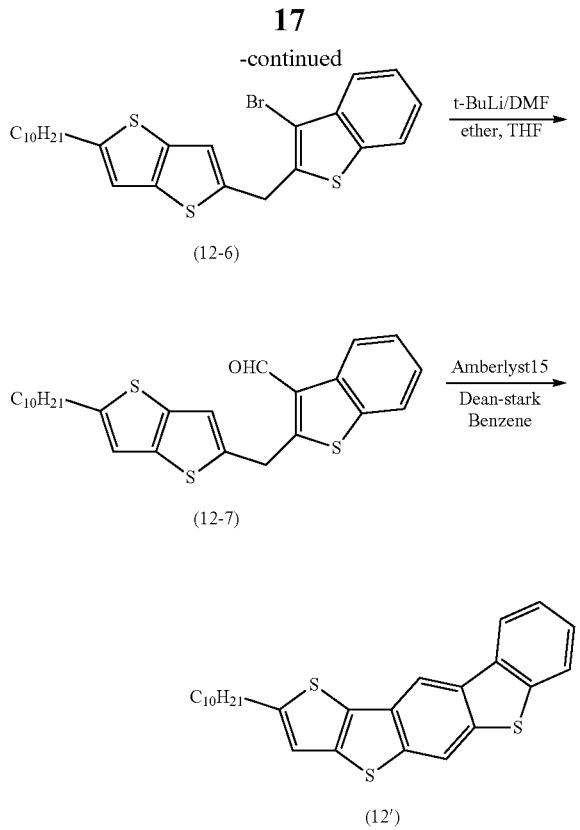

Synthesis of Intermediate (12-2):

Thienothiophene (thieno[3,2:b]thiophene, 90 g, 642 mmol) is dissolved in 500 mL of dry tetrahydrofuran (THF), the solution is added in a dropwise fashion to 1000 mL of a dry ether solution including butyl lithium (2.5 M in 270 mL of a hexane solution) cooled down to 0° C., and the mixture is agitated at room temperature for 2 hours while slowly increasing the temperature. 1-bromodecane (210 g, 950 mmol) is slowly added in a dropwise fashion to the murky solution, and the mixture is agitated overnight. 1000 mL of an ammonium chloride-saturated solution is added thereto, and a material precipitated therein is filtered and rinsed several times with water and ether, obtaining a desired intermediate (12-2) (a yield of 84%).

Synthesis of Intermediate (12-3):

The intermediate (12-2) (30 g, 107 mmol) is dissolved in 200 mL of dry ether, the solution is added in a dropwise fashion to 300 mL of a dry ether solution including butyl lithium (2.5 M in 64 mL of a hexane solution) cooled down to 0° C., and the mixture is agitated at room temperature for 1 hour while slowly increasing the temperature. The murky solution is cooled down to −78° C., DMF (dimethylformamide, 23 g, 308 mmol) is slowly added in a dropwise fashion, and the mixture is agitated for about 30 minutes. Herein, 200 mL of an ammonium chloride-saturated solution is added thereto, and a material precipitated therein is filtered and rinsed several times with water and ether, obtaining a desired intermediate (12-3) (a yield of 75%).

$^1$H NMR (300 MHz, CDCl$_3$): δ ppm 9.92 (s, 1H), 7.85 (s, 1H), 7.02 (s, 1H), 2.92 (t, 2H), 1.74 (m, 2H), 1.41-1.26 (m, 14H), 0.88 (t, 3H).

Synthesis of Intermediate (12-5):

3-bromobenzothiophene (the intermediate (12-4), 6.0 g, 28 mmol) is dissolved in 100 mL of dry tetrahydrofuran (THF), the solution is added in a dropwise fashion to 150 mL of a dry THF solution including LDA (lithium diisopropyl imide, 2.5 M in 15 mL of a hexane solution) cooled down to −78° C., and the mixture is agitated for 30 minutes. A solution prepared by dissolving the intermediate (12-3) (12 g, 40 mmol) in 30 mL of THF is added in a dropwise fashion to the solution, and the mixture is agitated for 30 minutes. Herein, 150 mL of an ammonium chloride-saturated solution is added thereto, and a material precipitated therein is filtered, and rinsed several times with water and ethyl acetate, obtaining a desired intermediate (12-5) (a yield of 75%).

$^1$H NMR (300 MHz, CDCl$_3$): δ ppm 7.82-7.78 (m, 2H), 7.47-7.37 (m, 2H), 7.20 (s, 1H), 6.90 (s, 1H), 6.95 (d, 1H), 2.84 (t, 2H), 2.74 (d, 2H), 1.68 (m, 2H), 1.42-1.25 (m, 14H), 0.87 (t, 3H).

Synthesis of Intermediate (12-6):

The intermediate (12-5) (11 g, 21 mmol) is dissolved in 500 mL of dichloromethane, and ZnI$_2$ (10.7 g, 33.6 mmol) and NaCNBH$_3$ (9.24 g, 147 mmol) are slowly added thereto. The mixture is agitated at room temperature for 24 hours, and then passed through a Celite pad. The filtered solution is respectively rinsed with the ammonium chloride-saturated solution and water, and then dried with MgSO$_4$ and concentrated under a reduced pressure, obtaining a yellow oil. This material is purified through silica chromatography, obtaining a desired intermediate (12-6) (a yield of 76%).

$^1$H NMR (300 MHz, CDCl$_3$): δ ppm 7.78-7.71 (m, 2H), 7.44-7.41 (m, 2H), 7.04 (d, 1H), 6.86 (d, 1H), 4.49 (d, 2H), 2.83 (t, 2H), 1.71-1.60 (m, 2H), 1.41-1.26 (m, 14H), 0.88 (t, 3H).

Synthesis of Intermediate (12-7):

A THF solution (100 mL) obtained by dissolving the intermediate (12-6) (8.0 g, 15.8 mmol) is added in a dropwise fashion to an ether solution (200 mL) including t-butyl lithium (24 mmol) dissolved therein and cooled down to −78° C. The mixture is agitated at −78° C. for about 30 minutes, DMF (3 g) is added thereto, and the resulting mixture is again agitated for about 2 hours. When the reaction is terminated by pouring water thereto, 200 mL of ethyl acetate is added thereto, the mixture is rinsed with water and brine to obtain an organic layer, and the organic layer is dried with MgSO$_4$ and concentrated under a reduced pressure, obtaining a colorless oil. This material is purified through silica chromatography, obtaining a desired intermediate (12-7) (a yield of 70%).

$^1$H NMR (300 MHz, CDCl$_3$): δ ppm 10.48 (s, 1H), 8.56 (d, 1H), 7.76 (d, 1H), 7.50-7.37 (m, 2H), 7.06 (s, 1H), 6.87 (s, 1H), 4.86 (s, 2H), 2.84 (t, 2H), 1.72-1.61 (m, 2H), 1.42-1.25 (m, 14H), 0.87 (t, 3H).

Figure 2:
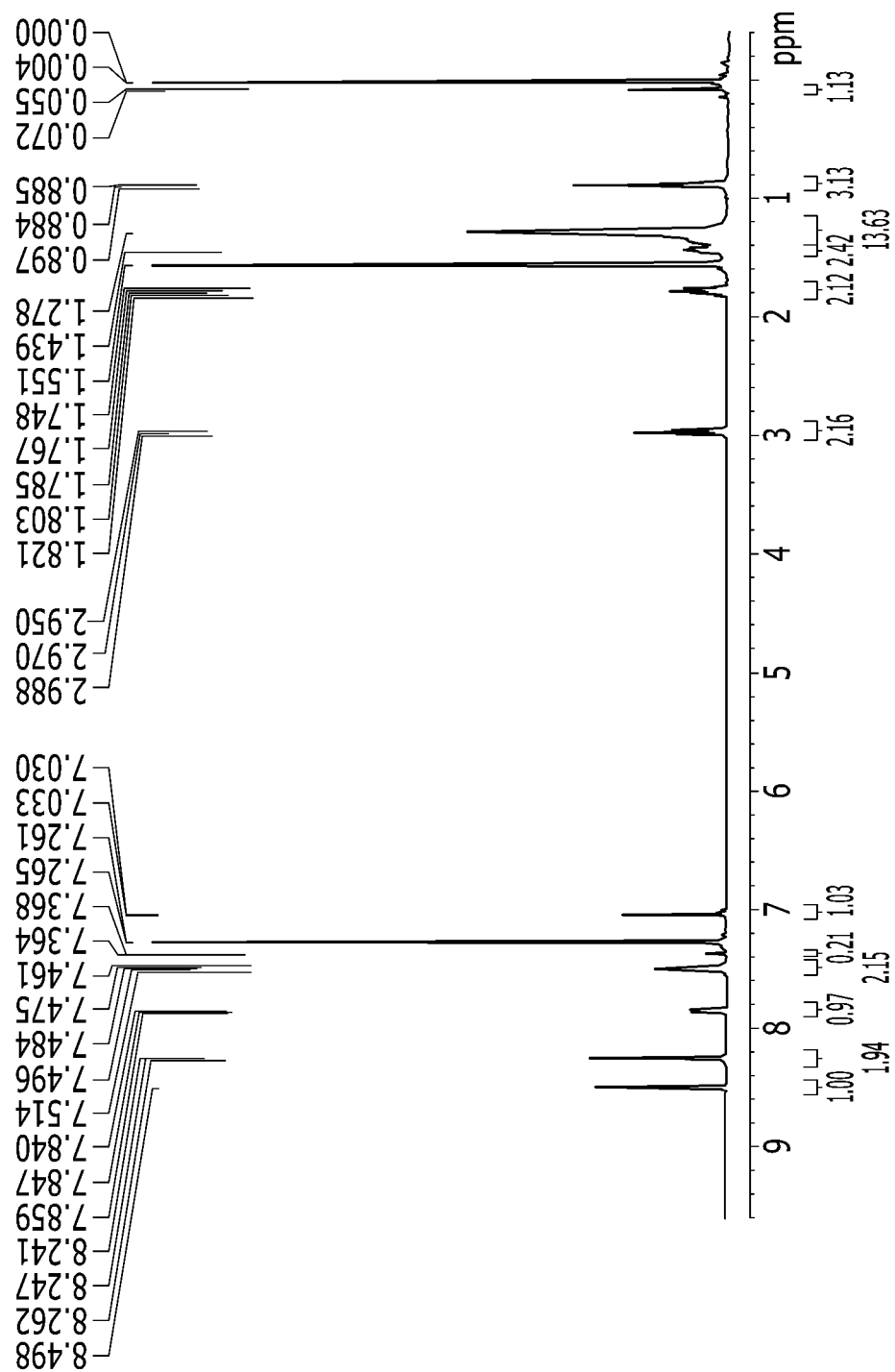
FIG. 2 is a $^1H$ NMR graph showing the compound (12') obtained in Example 2 according to example embodiments.

Synthesis of Compound (12'):

The intermediate (12-7) (4.54 g) is dissolved in 100 mL of benzene, Amberlyst 15 (3 g) is added thereto, and water therein is removed by using a Dean-Stark trap while the mixture is agitated and refluxed. About 24 hours later, the temperature is lowered down to room temperature, and the Amberlyst 15 is precipitated and filtered after skimming a floating material, obtaining a desired compound (12') as a yellow solid (a yield of 60%). FIG. 2 is a $^1$H NMR graph confirming that the resultant is the compound (12').

$^1$H NMR (300 MHz, CDCl$_3$): δ ppm 8.50 (a, 1H), 8.26-8.24 (m, 2H), 7.86-7.84 (m, 2H), 7.51-7.46 (m, 2H), 7.03 (d, 1H), 2.97 (t, 2H), 1.82-1.75 (m, 2H), 1.55-1.28 (m, 14H), 0.88 (t, 3H) (See FIG. 2).

EXAMPLE 3

Synthesis of Compound (13')

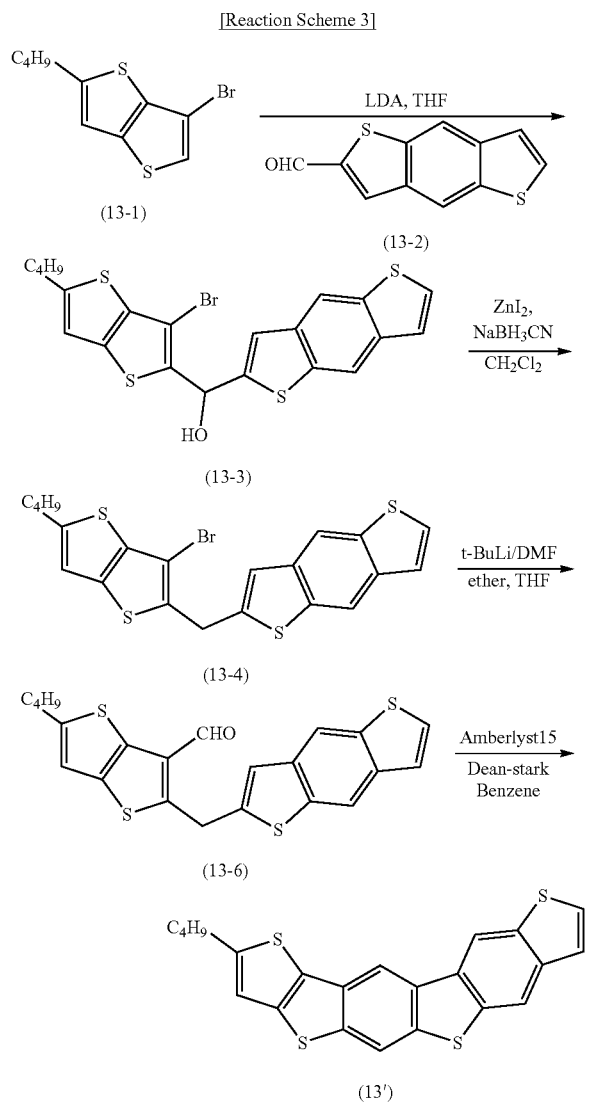

Synthesis of Intermediate (13-3):

6-bromo-2-butyl-thieno[3,2-b]thiophene 1, 6.0 g, 22 mmol) is dissolved in 100 mL dry THF, the solution is added in a dropwise fashion to 150 mL of a dry THF solution in which LDA cooled to −78° C. (lithium diisopropyl imide, 2.5 M in 12 mL of a hexane solution), and the resultant solution is agitated for 30 minutes. The intermediate (13-2) (7.4 g, 34 mmol) is added to 30 mL of THF and agitated for 30 minutes. 150 mL of a ammonium chloride saturated solution is added, a precipitate is filtered, and rinsed several times with water and ethyl acetate, obtaining a desired intermediate (13-3) (a yield of 75%). $^1$H NMR (300 MHz, CDCl$_3$): δ ppm 8.45 (s, 1H), 8.37 (s, 1H), 8.10 (s, 1H), 7.62 (d, 1H), 7.42 (d, 1H), 7.15 (s, 1H), 6.98 (s, 1H), 2.88 (m, 2H), 1.72 (m, 2H), 1.41-1.25 (m, 2H), 0.89 (t, 3H).

Synthesis of Intermediate (13-4):

The intermediate (13-3) (6.4 g, 13 mmol) is dissolved in 300 mL of dichloromethane (CH$_2$Cl$_2$), and ZnI$_2$ (6.4 g, 20 mmol) and NaCNBH$_3$ (5.5 g, 88 mmol) are slowly added thereto. The mixture is agitated at room temperature for 24 hours and then passed through a Celite pad. The filtered solution is respectively rinsed with the ammonium chloride-saturated solution and water, dried with MgSO$_4$, and concentrated under a reduced pressure, obtaining a yellow oil. This material is purified through silica chromatography, obtaining an intermediate (13-4) (a yield of 72%). $^1$H NMR (300 MHz, CDCl$_3$): δ ppm 8.44 (s, 1H), 8.36 (s, 1H), 8.11 (s, 1H), 7.61 (d, 1H), 7.40 (d, 1H), 7.15 (s, 1H), 6.98 (s, 1H), 4.50 (d, 2H), 2.85 (m, 2H), 1.71 (m, 2H), 1.25 (m, 2H), 0.88 (t, 3H).

Synthesis of Intermediate (13-5):

A THF solution (80 mL) prepared by dissolving the intermediate (13-4) (3.8 g, 8 mmol) is slowly added in a dropwise fashion to an ether solution (150 mL) including t-butyl lithium (24 mmol) dissolved therein and cooled down to −78° C. The mixture is agitated at −78° C. for about 30 minutes, DMF (2 g) is added thereto, and the resulting mixture is again agitated for about 2 hours. When the reaction is terminated by pouring water thereinto, 200 mL of ethyl acetate is added thereto and rinsed with water and brine to obtain an organic layer, and the organic layer is dried with MgSO$_4$ and concentrated under a reduced pressure, obtaining a colorless oil. This material is purified through silica chromatography, obtaining an intermediate (13-5) (a yield of 65%). $^1$H NMR (300 MHz, CDCl$_3$): δ ppm 10.43 (s, 1H), 8.44 (s, 1H), 8.36 (s, 1H), 8.11 (s, 1H), 7.65 (s, 1H), 7.61 (d, 1H), 7.40 (d, 1H), 6.98 (s, 1H), 4.87 (d, 2H), 2.84 (m, 2H), 1.65 (m, 2H), 1.28 (m, 2H), 0.88 (t, 3H).

Figure 3:
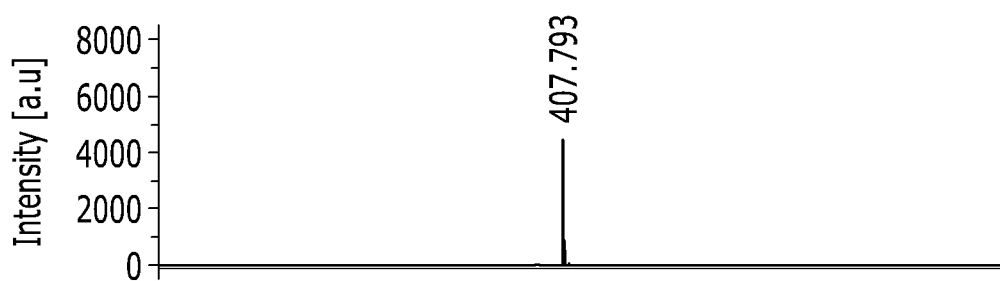
FIG. 3 is a Maldi-mass graph of the compound (13') according to Example 3.

Synthesis of Compound (13'):

The intermediate (13-5) (4.5 g) is dissolved in 100 mL of benzene, Amberlyst 15 (3 g) is added thereto, and water therein is removed by using a Dean-Stark trap while the mixture is agitated and refluxed. About 24 hours later, the temperature is lowered down to room temperature, and the Amberlyst 15 is precipitated and filtered after skimming a floating material, obtaining a desired compound (13') as a yellow solid (a yield of 60%). FIG. 3 is a Maldi-mass graph confirming that the resultant is the compound (13').

Example embodiments provide an organic thin film including the asymmetric fused polycyclic heteroaromatic compound and an electronic device including the organic thin film.

The organic thin film according to example embodiments includes the aforementioned asymmetric fused polycyclic heteroaromatic compound, and thus may be used as an organic semiconductor layer for an electronic device and a carrier transport layer (e.g., a channel layer), and the electronic device including the organic thin film shows improved electrical characteristics with higher charge mobility as well as improved processibility and workability.

Herein, the organic thin film may be manufactured by depositing more than one kind of the asymmetric fused polycyclic heteroaromatic compound on a substrate in a common method or dissolving it in an organic solvent and coating the solution in a common room temperature solution process, and the deposited or coated thin film may be heat-treated to increase density and uniformity thereof.

Particularly, the organic solvent may include at least one kind of general organic solvent, for example, at least one kind of an aliphatic hydrocarbon solvent (e.g., hexane and/or heptane); an aromatic hydrocarbon solvent (e.g., toluene, pyridine, quinoline, anisole, mesitylene and/or xylene); a ketone-based solvent (e.g., methyl isobutyl ketone, 1-methyl-2-pyrrolidinone, cyclohexanone and/or acetone); an ether-based solvent (e.g., tetrahydrofuran and/or isopropyl ether); an acetate-based solvent (e.g., ethyl acetate, butyl acetate and/or propylene glycol methyl ether acetate); an alcohol-based solvent (e.g., isopropyl alcohol and/or butanol); an amide-based solvent (e.g., dimethyl acetamide and/or dimethyl formamide); a silicone-based solvent; and a mixture of solvents. The amount of the asymmetric fused polycyclic heteroaromatic compound dissolved in the organic solvent may be appropriately selected and determined by a person of ordinary skill in the art, for example, in a range of about 0.01 wt % to about 50 wt % in the total solvent in view of solubility and coating property.

The method of providing an organic thin film may include thermal deposition, vacuum deposition, laser deposition, screen printing, printing, imprinting, spin casting, dipping, ink jetting, roll coating, flow coating, drop casting, spray coating, and/or roll printing, but is not limited thereto. The heat treatment may be performed at about 80 to about 250° C. for about 1 minute to about 2 hours, but is not limited thereto.

The thickness of the organic thin film may be adjusted according to the usage and the case considering the kinds of the used compound and solvent by a person of ordinary skill in the art, and is specifically in a range of about 200 Å to about 10,000 Å.

Examples of electronic devices including the organic thin film as a carrier transport layer may include a transistor, an organic light emitting diode (OLED), a photovoltaic device, a solar cell, a laser device, a memory, and/or a sensor, and the organic thin film may be applied to each device according to the general process commonly known in the art.

For example, the transistor includes a gate electrode disposed on a substrate; a source electrode and a drain electrode facing each other and defining a channel region; an insulation layer electrically insulating the source electrode and drain electrode and the gate electrode; and an active layer including the asymmetric fused polycyclic heteroaromatic compound formed in the channel region.

The active layer may be obtained by depositing the fused polycyclic heteroaromatic compound, or applying a composition including the asymmetric fused polycyclic heteroaromatic compound to a solution process, for example, screen printing, printing, spin coating, dipping, and/or ink jetting. When the active layer is formed by the solution process, the process cost may be reduced, and a wider area device may be effectively manufactured.

Figure 4:
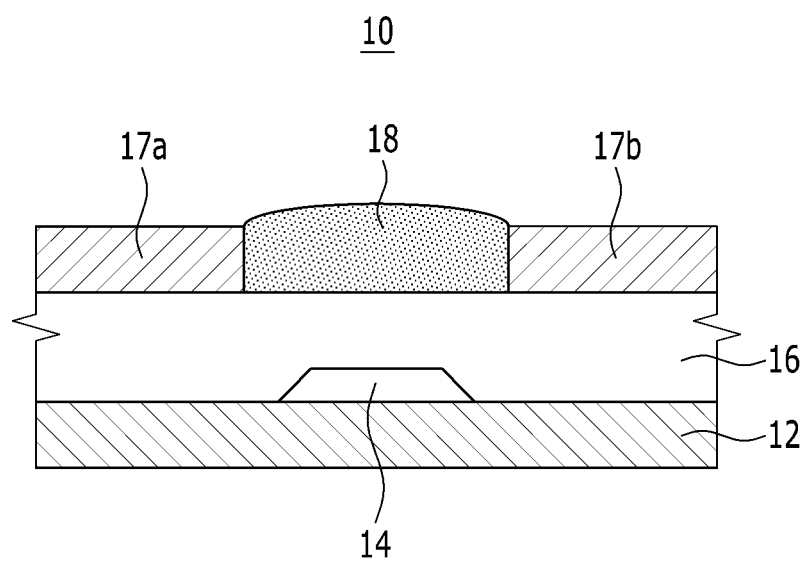
FIG. 4 is a schematic cross-sectional view showing a transistor according to example embodiments.
Figure 5:
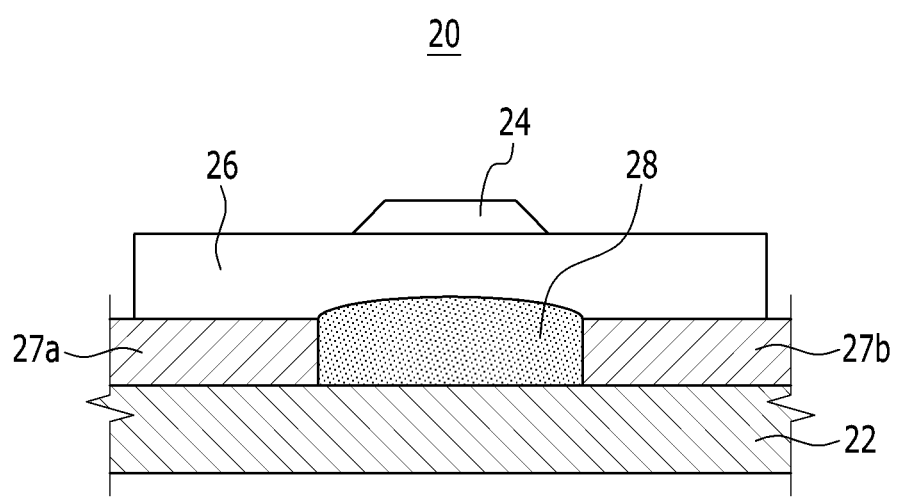
FIG. 5 is a schematic cross-sectional view showing a transistor according to example embodiments.

FIGS. 4 and 5 are schematic cross-sectional views showing a transistor according to example embodiments. The transistor according to example embodiments may be a thin film transistor. The thin film transistor may be a thin film having a thickness of several nanometers to several microns.

Referring to FIG. 4, a transistor 10 includes a substrate 12, a gate electrode 14 disposed on the substrate, and an insulation layer 16 covering the gate electrode 14. A source electrode 17a and a drain electrode 17b defining a channel region are provided on the insulation layer 16, and an active layer 18 is provided in the channel region. The active layer 18 includes the asymmetric fused polycyclic heteroaromatic compound.

Referring to FIG. 5, a transistor 20 includes a source electrode 27a and a drain electrode 27b defining a channel region and that are formed on a substrate 22, and an active layer 28 formed on the channel region. The active layer 28 includes the asymmetric fused polycyclic heteroaromatic compound. An insulation layer 26 is formed to cover the source electrode 27a, the drain electrode 27b, and the active layer 28, and a gate electrode 24 is formed thereon.

The substrates 12 and 22 may include an inorganic material, an organic material, or a composite of an inorganic material and an organic material. The organic material may include, for example, a plastic (e.g., polyethylene naphthalate (PEN), polyethylene terephthalate (PET), polycarbonate, polyvinyl alcohol, polyacrylate, polyimide, polynorbornene, and polyethersulfone (PES)), and the inorganic material may include, for example, glass or metal.

In addition, the gate electrodes 14 and 24, source electrodes 17a and 27a, and drain electrodes 17b and 27b may include a generally-used metal, particularly, gold (Au), silver (Ag), aluminum (Al), nickel (Ni), or indium tin oxide (ITO), but it is not limited thereto.

The insulation layers 16 and 26 may include a generally-used insulator having a high dielectric constant, for example, a ferroelectric insulator (e.g., $Ba_{0.33}Sr_{0.66}TiO_3$ (BST, barium strontium titanate), $Al_2O_3$, $Ta_2O_5$, $La_2O_5$, $Y_2O_3$ and/or $TiO_2$); an inorganic insulator (e.g., $PbZr_{0.33}Ti_{0.66}O_3$ (PZT), $Bi_4Ti_3O_{12}$, $BaMgF_4$, $SrBi_2(TaNb)_2O_9$, $Ba(ZrTi)O_3$ (BZT), $BaTiO_3$, $SrTiO_3$, $SiO_2$, $SiN_X$ (x is determined depending on valence of Si), and/or AlON (aluminum oxynitride)); or an organic insulator (e.g., polyimide, benzocyclobutane (BCB), parylene, polyacrylate, polyvinyl alcohol, and polyvinylphenol), but it is not limited thereto. Although it is not mentioned above, the inorganic insulator disclosed in U.S. Pat. No. 5,946,551 and the organic insulator disclosed in U.S. Pat. No. 6,232,157 may be used for the insulation layers 16 and 26.

While this disclosure has been described in connection with what is presently considered to be practical example embodiments, it is to be understood that the present inventive concepts are not limited to the disclosed embodiments, but, on the contrary, is intended to cover various modifications and equivalent arrangements included within the spirit and scope of the appended claims.

What is claimed is:

1. A fused polycyclic heteroaromatic compound represented by the following Chemical Formulae 1A to 1B:

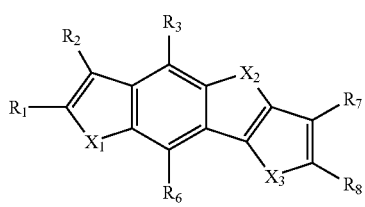

[Chemical Formula 1A]

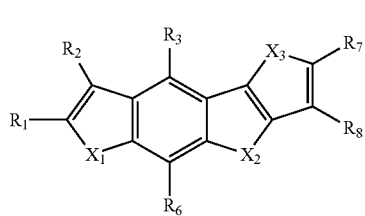

[Chemical Formula 1B]

wherein, in the Chemical Formulae 1A and 1B, each of $X_1$, $X_2$, and $X_3$ are independently one of O, S, Se, Te, and N—$R^a$, each of $R_3$, $R_6$ to $R_8$, and $R^a$ are independently one of hydrogen, a linear or branched $C_1$ to $C_{30}$ alkyl group, a $C_7$ to $C_{30}$ arylalkyl group, a $C_6$ to $C_{30}$ aryl group, a $C_1$ to $C_{30}$ alkoxy group, a $C_6$ to $C_{30}$ aryloxy group (—$OR^b$, wherein $R^b$ is a $C_6$ to $C_{30}$ aryl group), a $C_4$ to $C_{30}$ cycloalkyl group, a $C_4$ to $C_{30}$ cycloalkyloxy group (—$OR^c$, wherein $R^c$ is a $C_4$ to $C_{30}$ cycloalkyl group), a $C_2$ to $C_{30}$ heteroaryl group, and a halogen, and $R_1$ and $R_2$ are linked to each other to provide one of a substituted or unsubstituted $C_6$ to $C_{30}$ aromatic ring and a $C_2$ to $C_{30}$ hetero aromatic ring except a thiophene ring, wherein the fused polycyclic heteroaromatic compound has an asymmetric structure.

2. The fused polycyclic heteroaromatic compound of claim 1, wherein the fused polycyclic heteroaromatic compound is represented by the following Chemical Formulae 1K or 1L:

[Chemical Formula 1K]

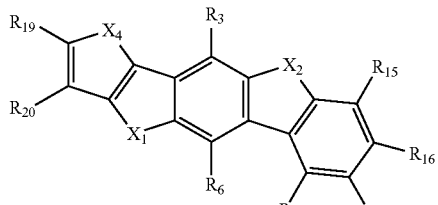

[Chemical Formula 1L]

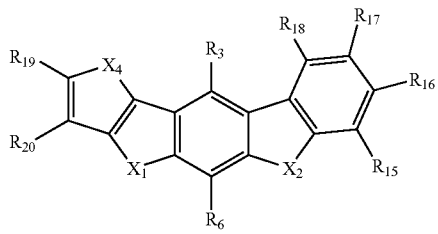

wherein, in the Chemical Formulae 1K and 1L, each of $X_1$, $X_2$, and $X_4$ are independently one of O, S, Se, Te, and N—$R^a$, each of $R_3$, $R_6$, $R_{15}$ to $R_{20}$, and $R^a$ are independently one of hydrogen, a linear or branch $C_1$ to $C_{30}$ alkyl group, a $C_7$ to $C_{30}$ arylalkyl group, a $C_6$ to $C_{30}$ aryl group, a $C_1$ to $C_{30}$ alkoxy group, a $C_6$ to $C_{30}$ aryloxy group (—$OR^b$, wherein $R^b$ is a $C_6$ to $C_{30}$ aryl group), a $C_4$ to $C_{30}$ cycloalkyl group, a $C_4$ to $C_{30}$ cycloalkyloxy group (—$OR^c$, wherein $R^c$ is a $C_4$ to $C_{30}$ cycloalkyl group), a $C_2$ to $C_{30}$ heteroaryl group, and a halogen.

3. The fused polycyclic heteroaromatic compound of claim 1, wherein the fused polycyclic heteroaromatic compound has an average molecular weight of about 350 to about 3000.

4. An organic thin film comprising the fused polycyclic heteroaromatic compound of claim 1.

5. An electronic device comprising the fused polycyclic heteroaromatic compound of claim 1.

6. The electronic device of claim 5, wherein the electronic device is one of a transistor, an organic light emitting diode (OLED), a photovoltaic device, a solar cell, a laser device, a memory, and a sensor.

7. The electronic device of claim 5, wherein
the electronic device includes at least one charge transport layer, and
the fused polycyclic heteroaromatic compound is included in the charge transport layer.

* * * * *